United States Patent [19]

Puglia et al.

[11] 4,327,076

[45] Apr. 27, 1982

[54] COMPRESSED CHEWABLE ANTACID TABLET AND METHOD FOR FORMING SAME

[75] Inventors: Wayne J. Puglia, Bellerose Village; Kanit J. Patanasinth, Tarrytown; Andrew T. Lombardo, Bronx, all of N.Y.; John E. Beam, Norwalk, Conn.; Donald A. M. Mackay, Pleasantville, N.Y.

[73] Assignee: Life Savers, Inc., New York, N.Y.

[21] Appl. No.: 207,157

[22] Filed: Nov. 17, 1980

[51] Int. Cl.³ .................. A61K 9/20; A61K 9/42; A61K 33/08; A61K 33/10

[52] U.S. Cl. ................... 424/38; 424/154; 424/155; 424/156; 424/157; 424/158; 424/147; 424/230; 424/252; 424/255; 424/263; 424/266; 424/280; 424/361; 424/362; 424/365; 426/660

[58] Field of Search ............... 424/38, 154–158, 424/361, 362, 365

[56] References Cited

U.S. PATENT DOCUMENTS

| 780,226 | 1/1905 | Pink | 424/38 |
|---|---|---|---|
| 3,253,988 | 5/1966 | Scott | 424/154 |
| 3,384,546 | 5/1968 | Palermo | 424/156 |
| 3,452,138 | 6/1969 | Granatek et al. | 424/156 |
| 3,536,074 | 10/1970 | Auf Hauser | 424/38 |
| 3,843,778 | 10/1974 | Diamond et al. | 424/38 |
| 4,112,066 | 9/1978 | Hussein | 424/48 |
| 4,115,553 | 9/1978 | Rubino et al. | 424/156 |
| 4,163,777 | 8/1979 | Mitra | 424/21 |
| 4,199,560 | 4/1980 | Gyarmati et al. | 424/19 |
| 4,230,693 | 10/1980 | Izzo et al. | 424/156 |
| 4,271,142 | 6/1981 | Puglia et al. | 424/14 |

FOREIGN PATENT DOCUMENTS

| 8869 | of 1888 | United Kingdom | 424/15 |
|---|---|---|---|
| 26894 | of 1908 | United Kingdom | 424/156 |
| 392 | of 1913 | United Kingdom | 424/156 |
| 543309 | 2/1942 | United Kingdom | 424/38 |
| 1414121 | 11/1975 | United Kingdom | 424/157 |
| 1538280 | 1/1979 | United Kingdom | . |

*Primary Examiner*—Shep K. Rose
*Attorney, Agent, or Firm*—Richard Kornutik

[57] ABSTRACT

An improved compressed soft chewable tablet is provided, which may contain an antacid or other active ingredient, has good flexibility, is breakage resistant and disintegrates immediately upon chewing. The tablet of the invention is formed of particles of antacid and/or other active ingredient which are isolated from other ingredients of the tablet, preferably by admixing particles of active ingredient with particles formed of edible fat or oil absorbed on a fat-absorbing material, such as microcrystalline cellulose and blending such particles with one or more tablet bonders; the tablet also includes additional amounts of tablet bonders, flavors and other conventional tabletting aids to help in making the tablet more palatable. Upon chewing, the tablet is quickly converted to a smooth creamy non-gritty palatable emulsion.

5 Claims, No Drawings

COMPRESSED CHEWABLE ANTACID TABLET AND METHOD FOR FORMING SAME

CROSS REFERENCE TO RELATED APPLICATIONS

This application contains subject matter related to, but distinctly different from, the subject matter of U.S. Pat. No. 4,271,142 based on U.S. application Ser. No. 170,469, filed July 21, 1980, to Puglia et al, U.S. application Ser. No. 137,944 to Witzel et al, filed Apr. 7, 1980 and U.S. application Ser. No. 175,179 to Morris et al, filed Aug. 4, 1980.

The present invention relates to a compressed chewable tablet, such as an antacid tablet, which is breakage resistant, yet quickly disintegrates in the mouth to a smooth creamy pleasant-tasting emulsion, devoid of the grittiness normally associated with antacids.

BACKGROUND OF THE INVENTION

Palatability and "mouth feel" are extremely important factors in formulating chewable tablets, especially pharmaceutical dosage forms. Many pharmaceutical and confectionery tablets are designed to be chewed either to provide proper flavorants or to increase the surface area of a particular drug to permit rapid activity in the digestive or circulatory system. Consequently, tablet formulations must be developed which will satisfy certain basic requirements:

sufficient cohesive properties to form a firm tablet under compression
sufficient lubrication to prevent binding in the die cavities
adequate flow to provide uniform weight
absence of sticking under compression
uniform drug dose and release after ingestion
production capability on high speed equipment Furthermore, many pharmaceutical ingredients usually have both an unpleasant mouth feel and unpalatable taste due to chalkiness, grittiness, dryness and astringent properties of these materials. Accordingly, the practical value of these materials is substantially diminished since patients finding them objectionable may fail to take them as prescribed.

In an effort to overcome the above problems, flavorings have been employed with pharmaceuticals and especially antacids and vitamins to either mask or override the unpleasant dryness and astringent properties and chalkiness associated therewith. Unfortunately, it has been found that the flavoring merely masks the unpleasant taste, but the chalkiness, grittiness, dryness and astringent properties still remain.

U.S. Pat. No. 3,843,778 to Diamond et al discloses a technique for coating antacid particles with a water insoluble, inert, non-toxic hydrocarbon oil which is formulated into suspensions or tablets which are said to be substantially free of the impalatable "mouth feel" properties associated with antacids. An electronegative agent, such as a surfactant selected from an alkyl aryl sulfonate, or an alkyl sulfate or sulfonate, or sulfonated amides or amines, or sulfated or sulfonated esters or ethers, or a dioctyl sulfosuccinate, or a hydrated aluminum silicate, such as bentonite or kaolin, is employed to aid in adhering the oil to the electropositively charged antacid particles.

U.S. Pat. No. 3,253,988 to Scott discloses an orally administrable antacid formed of oils or fats, that is, esters of higher fat acids and a trihydric alcohol, in combination with antacids. The Scott antacid may be in the form of a waxy solid, an emulsion or suspension and is apparently prepared by simply homogeneously blending all of the ingredients.

British Pat. No. 1,538,280 to Armour-Dial, Inc. describes an antacid tablet containing fat, antacid, sugar, starch and water. It is prepared through a wet granulation technique and utilizes fats with melting points above body temperature. Also, the tablet press employed must be heated to 105°–120° F. to avoid sticking and adherence to punch faces. The antacid tablet is said to be prepared by mixing the antacid ingredient, water, sugar and fat to provide a powdered mixture, forming the mixture into a tablet shape and applying a pressure of from 50 to 600 psi to the mixture, the tabletting machine, including the punch elements of the presses, preferably being maintained at an elevated temperature.

The tablet may also be prepared by mixing the fat in liquid form and the antacid with the sugar and water, cooling the resultant mixture to a temperature of below 40° F. and then passing the mixture through a mill to obtain a powdered mixture which is then formed into tablets.

Generally, tablets are normally made by direct compression wherein a mixture of tabletting compounds including active ingredient, flavor, bonders, etc., are fed to a die chamber of a tablet press and a tablet is formed by direct compaction. Hardness of the resulting tablet is a direct function of the compression pressure employed. Where it has been desired to produce a so-called "soft" tablet, that is one which has easy bite-through, a disintegrator, such as alginic acid, is added to the pre-tablet mix. Alternatively, a soft tablet has been formed by employing reduced compression temperatures. The result in each instance has been essentially the same, namely, production of a softer tablet which is very fragile and brittle and is easily chipped.

It has also been suggested to employ a fatty material in the pre-tablet mix to attain tablet softness. However, it has been found that the addition of fats or oils to the pre-tablet mix causes tabletting ingredients to adhere to the die chamber and significant reduction in the bonding action of the bonders present in the mix.

DESCRIPTION OF THE INVENTION

In accordance with the present invention, a unique compressed chewable tablet is provided which has excellent hardness and flexibility, is breakage and chip resistant and yet may be easily chewed and quickly disintegrated and dissolved in the mouth. The compressed chewable tablet of the invention includes (a) a particulate pretreated fat composition formed of an edible fatty material, a fat-sorbing material having the fatty material sorbed thereon or therein, and one or more tablet bonders blended therewith, and optionally one or more antioxidants, flavors and/or colorant; (b) a pretreated active ingredient composition formed of a mixture of particles of active ingredient, such as particles of one or a mixture of antacids, and optionally edible oil, binder, emulsifier, flavor, and colorant, the particles of active ingredients being coated with the other components of said pretreated active ingredient composition; and (c) a pretreated direct compaction tabletting aids composition including bonders and optionally flavors, the compositions (a), (b) and (c) being blended together and the blend being in the form of said compressed chewable tablet.

In a preferred embodiment of the compressed chewable tablet of the invention, the active ingredient is comprised of particles of one or more antacids so that the particulate pretreated fat composition (a) will include a fat-sorbing material, preferably microcrystalline cellulose, a fatty material absorbed in the microcrystalline cellulose, optionally a colorant, such as titanium dioxide, optionally an antioxidant, such as butylated hydroxytoluene, optionally an antiflatulent, such as simethicone, tablet bonders, preferably tabletting sugar and/or dextrose monohydrate, and optionally one or more flavors.

The preferred pretreated active ingredient composition (b) will include particles of one or more antacids, such as calcium carbonate, aluminum hydroxide and/or magnesium hydroxide, and preferably a mixture of all of said antacids, a binder, preferably carboxymethyl cellulose, to help flavor and emulsifier to stick to fat absorbed particles and impart a slippery mouth feel, an emulsifier, such as polyglycerol ester of fatty acids, to help decrease surface tension on the tongue and stimulate salivation, an edible oil, preferably a vegetable oil, to help plating out of the emulsifier on the antacid particles, and flavor.

The preferred pretreated direct compaction tabletting aids composition (c) will include tablet bonders, preferably tabletting sugar and/or dextrose monohydrate, and flavors and flavor oils.

It is essential in forming the compressed chewable tablets of the invention that the edible fatty material which imparts good softness, flexibility and taste to the tablets of the invention be isolated from the other ingredients and, in fact, be in such a state that it will not gum up the die chamber of the tablet press or negate the bonding action of the tablet bonders present. This is accomplished through the method of the present invention for forming the above-described compressed chewable tablets which includes the following steps:

forming the particulate pretreated fat composition (a) by melting the edible fatty material, admixing the melted fatty material with colorant, if present, and antioxidant, if present, admixing the resulting mixture with the fat-sorbing material thereby causing the fatty material to be sorbed in the fat-sorbing material, the mixture at this juncture exhibiting the appearance of a fatty powder, allowing the resulting mixture to dry and harden, and after sifting the mixture, blending same with one or more tabletting bonders and flavors, if present, to form the particulate pretreated fat composition (a);

forming the pretreated active ingredient composition (b) by blending particles of active ingredient and binder, separately blending together one or more emulsifiers, edible oil, and flavor, if present, and blending each of the above mixtures until a free-flowing powder is obtained wherein said particles of active material are coated with binder, oil, flavor and emulsifier;

forming the pretreated direct compaction tabletting aids composition by mixing one or mre tablet bonders with one or more flavors;

blending the above mixes; and forming a compressed tablet from the resulting mixture.

The finished tablets hardness of the tablets so-produced is not directly related to compression pressure. In fact, tablets produced under medium or high pressure (for example, employing pressures of from about 4,000 to about 10,000 psi), in accordance with the method of the present invention, have excellent hardness and flexibility, and lack of brittleness, but are still easily chewed and dissolved in the mouth.

The compressed chewable tablet of the invention includes particles of active ingredient, such as antacids, vitamins, laxatives, antiflatulents, aspirin, acetaminophen, appetite depressants and the like and will have a non-chalky non-gritty pleasant taste and when exposed to saliva in the mouth converts to an emulsion or colloidal suspension and thus behaves as would a liquid. Also, since the tablet of the invention will disintegrate rapidly in hot solution, it would be an advantageous portable vehicle for flavoring beverages where the inclusion of a fat or fat based system would improve palatibility. Examples of such vehicles would be tabletted coffee whiteners and flavorants, bouillon type soups, cream type soups, and the like.

The active ingredient, depending upon the specific properties thereof, will generally comprise from about 90 to about 99.9% and preferably from about 92 to about 97% by weight of the pretreated active ingredient composition, and from about 10 to about 50% and preferably from about 15 to about 30% by weight of the final tablet.

As indicated, in preferred embodiments, the active ingredient will be an antacid material which will be present in an amount within the range of from about 10 to about 50% by weight and preferably from about 15 to about 30% by weight of the final tablet. Examples of antacids suitable for use herein comprise any relatively water insoluble antacid acceptable to the Food and Drug Administration, such as, aluminum carbonate, aluminum hydroxide (or as aluminum hydroxide—hexitol stabilized polymer, aluminum hydroxide—magnesium hydroxide codried gel, aluminum hydroxide—magnesium trisilicate codried gel, aluminum hydroxide—sucrose powder hydrated), aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

Preferred antacids include aluminum hydroxide, calcium carbonate, magnesium carbonate and mixtures thereof as well as magnesium hydroxide.

The fats or oils used may be of animal, vegetable or mineral origin which are substantially water-insoluble, inert, non-toxic hydrocarbon fats and oils and derivatives thereof and may comprise any of the commonly commercially available fats or oils approved by the Food and Drug Administration and having melting points constant with desired mouth feeling factors, such as melting points ranging from 80° to 110° F. and need not be limited to melting points above body temperature. The fats or oils will be employed in amounts within the range of from about 2 to about 45%, and preferably from about 10 to about 25%, depending upon the properties desired in the final product. Examples of fats and/or oils suitable for use herein include hydrogenated tallow, hydrogenated vegetable oil, almond oil, coconut oil, corn oil, cottonseed oil, refined linseed oil, light liquid petrolatum, heavy liquid petrolatum, olein, olive oil, palm oil, peanut oil, persic oil, sesame oil, soybean oil or safflower oil.

Preferred oils include corn oil, light and heavy liquid petrolatum, olein, olive oil, peanut oil and soybean oil.

The fat-sorbing materials (that is, fat-absorbing and/or fat-adsorbing material) which may be present herein include microcrystalline cellulose, cornstarch, tapioca, dextrin, sucrose, sorbitol, xylitol, mannitol and the like with microcrystalline cellulose being preferred. The fat-sorbing material will be present in the pretreated fat composition in an amount of from about 25 to about 75% and preferably from about 40 to about 60% by weight of said pretreated fat composition and will be employed in a weight ratio of the fatty material of from about 0.625:1 to about 1.815:1 and preferably from about 1:1 to about 1.5:1; the fat-sorbing material will be present in the finished tablet formulation in an amount of from about 10 to about 30% and preferably from about 10 to about 20% by weight.

The fat-sorbing material will preferably be in finely-divided form and as such will have a preferred average particle size of 90 microns plus or minus 20 microns.

As indicated, the pretreated fat composition and the pretreated mixture of tabletting aids will include tablet bonders examples of which include sugars, sugar alcohols, and mixtures thereof, such as dextrose hydrate (such as Cerelose 2043), corn syrup solids having a dextrose equivalent (D.E.) ranging from 38 to 45, lactose, mannitol, sorbitol, xylitol, sucrose and invert sugar, and mixtures thereof, with tabletting sugar, dextrose monohydrate and mixtures thereof being peferred. The total amount of bonders present will range from about 20 to about 60% and preferably from about 30 to about 40% by weight of the final tablet, with the pretreated fat composition containing from about 10 to about 50%, and preferably from about 20 to about 30% by weight bonders, and the pretreated tabletting aids composition containing from about 90 to about 99.9%, and preferably from about 97 to about 99.5% bonders.

The edible oil in the pretreated active ingredient composition, which aids in plating out emulsifier on particles of active ingredient, will be present in an amount within the range of from about 1 to about 4%, and preferably from about 1.5 to about 2.5% and may include any of the edible oils disclosed with respect to the fatty materials set out above.

Any emulsifier or surfactant approved for use in foods by the Food and Drug Administration and having an HLB value of 8 and above, may be employed in the pretreated active ingredient composition in forming antacid tablets of the invention in amounts ranging from about 0.05 to about 2.5% by weight and preferably in amounts ranging from about 0.1 to about 1.0% by weight based on the final tablet formulation, and from about 1 to about 4% and preferably from about 1.5 to about 2.5% based on the weight of the pretreated active ingredient composition.

Examples of emulsifiers or surfactants suitable for use herein to aid in release of the antacid ingredient include alkyl aryl sulfonate, or alkyl sulfates, or sulfonated amides or amines, or sulfated or sulfonated esters or ethers, or alkyl sulfonates, or dioctyl sulfosuccinate and the like, or a hydrated aluminum silicate such as micronized bentonite or kaolin, or Cab-O-Sil (which is silica pigment sold under the trademark of Cab-O-Sil by Cabot Corporation of Boston, Mass.), Quso (which is a microfine silica sold under the trademark Quso by Philadelphia Quartz Co. of Philadelphia, Pa.), and the like, triglycerol monostearate, triglycerol monoshortening, octaglycerol monooleate, octaglycerol monostearate, decaglycerol decaoleate, Span 60, and Tween 60 and 80.

Preferred are the polyoxyethylene sorbitan fatty acid esters, such as the stearates, oleates, palmitates and the like, for example Tween 60 and 80, as well as octaglycerol monooleate, triglycerol monostearate and triglycerol monoshortening.

The slip agent present in the pretreated active ingredient composition includes cellulose gums, such as carboxymethyl cellulose gum, xanthan gum, locust bean gum, alginic acid, or mixtures thereof and will be present in an amount of within the range of from about 1 to about 5% by weight of the pretreated active ingredient composition, and from about 2.5 to about 3.5%, and preferably from about 0.75 to about 1.5% based on the weight of the finished tablet.

The essential ingredient present for masking chalkiness, grittiness, dryness and astringent properties in the preferred antacid tablet of the invention will be a natural or synthetic fatty type or other flavorant, examples of which include cocoa, chocolate, especially mint chocolate, butter, milk, cream, vanillin butter fat, egg or egg white, as well as peppermint oil, wintergreen oil, spearmint oil and the like, with the chocolate or vanilla being preferred. Where the above flavorant is employed in amounts within the range of from about 0.05 to about 1% and preferably from about 0.5 to about 0.8% by weight of the tablet, the flavorant, together with the fat and/or oil provides a synergistic effect in minimizing grittiness and enhancing texture and mouth feel.

The fatty materials comprising the above flavors may be employed as the fatty material in the pretreated fat composition; further, flavors will be present in each of the three pretreated compositions discussed above, with the bulk of the flavors being present in the pretreated tabletting aids composition.

The antacid tablet of the invention may also include other pharmaceutically acceptable agents, such as sweetening agents, including sugars, sugar alcohols, hydrogenated starch hydrolysates (Lycasin) and synthetic sweeteners, such as sorbitol, xylitol, saccharin salts, free acid form of saccharin, cyclamate salts, free cyclamic acid, dihydrochalcones, L-aspartyl-L-phenylalanine methyl ester, isomaltitol (Palatinit), as well as coloring agents, other flavoring agents, disintegrating agents, such as starch, other binding agents, lubricants, such as calcium stearate, stearic acid, magnesium stearate (0.5 to 3% by weight), antioxidants, such as butylated hydroxy toluene, antiflatulents, such as simethicone and the like.

In addition, the antacid tablet may be sealed in a sealant, such as gum arabic or starch to prevent breakage. Furthermore, the tablet may be spray coated or otherwise coated with chocolate or other standard confections coating to prevent breakage during shipment and handling and to further decrease the chalky nature of the tablet. In addition, a confections glaze may be applied over the coating to prevent premature melting during handling.

It is preferred that in formulating the antacid tablet of the invention that the antacid material have a primary particle size of less than 100 millimicrons and more preferably less than 50 millimicrons, and that where mixing is required during the preparation of the antacid tablet that the antacid material, fat or oil, flavorant, and other ingredients be intensively mixed until complete homogeneity is achieved in each step.

The following are preferred chewable tablet formulations in accordance with the present invention:

| | | % by Wt. based on pretreated composition | % by Wt. based on total tablet |
|---|---|---|---|
| I. | Pretreated Fat Composition | | |
| (a) | Fatty material (preferably hydrogenated vegetable oil) | 30 to 50 | 10 to 20 |
| (b) | Fat-sorbing material (preferably microcrystalline cellulose) | 25 to 35 | 10 to 15 |
| (c) | Tabletting bonders (preferably tabletting sugar and dextrose monohydrate) | 20 to 30 | 7.5 to 15 |
| (d) | Flavor | 0.1 to 0.4 | 0.05 to 0.15 |
| (e) | Colorant | 0.05 to 0.4 | 0.1 to 0.3 |
| (f) | Antioxidant | 0.05 to 0.1 | 0.01 to 0.03 |
| | Pretreated | | |
| II. | Active Ingredient Composition | | |
| (g) | Active ingredient (Preferably antacid CaCO$_3$ | 50 to 60 | 10 to 15 |
| | Al(OH)$_3$ | 15 to 25 | 3 to 6 |
| | Mg(OH)$_2$) | 15 to 25 | 3 to 6 |
| (h) | Slip agent (preferably carboxymethyl cellulose) | 1.5 to 4 | 0.5 to 1.5 |
| (i) | Emulsifier (preferably polyglycerol ester of fatty acid) | 1 to 3 | 0.25 to 0.75 |
| (j) | Edible oil (preferably hydrogenated vegetable oil) | 1 to 3 | 0.25 to 0.75 |
| (k) | Flavor | 0.2 to 0.5 | 0.05 to 0.15 |
| | Pretreated | | |
| III. | Tabletting Aids Composition | | |
| (l) | Tablet bonders (preferably tabletting sugar and dextrose monohydrate) | 95 to 99.9 | 30 to 40 |
| (m) | Flavor | 1.5 to 5 | 0.1 to 1 |

The following Examples represent preferred embodiments of the present invention.

EXAMPLE 1

A chewable antacid tablet is prepared as described below from the following three premixes.

| Premix I (Pretreatment of Fat System) | Parts by Weight of Total Tablet |
|---|---|
| 1. Hydrogenated vegetable oil (Satina II NT) | 16.225 |
| 2. Microcrystalline cellulose (Avicel pH 102 - particle size 90μ) | 12.27 |
| 3. Titanium dioxide (colorant) | 0.03 |
| 4. Simethicone LVA (antiflatulent) | 1 |
| 5. Dextrose monohydrate (Cantab) | 10 |
| 6. Artificial vanilla flavor | 0.1 |
| 7. Butylated hydroxytoluene (antioxidant) | 0.01 |

The above premix I is prepared as follows.

The titanium dioxide, Santina II$^{NT}$ (fat), simethicone and butylated hydroxytoluene are heated under agitation to 140° F. The mixture is transferred to a Hobart mixer and the microcrystalline cellulose is added under agitation. Upon mixing, the microcrystalline cellulose absorbs its weight of fat so that the mixture exhibits the appearance of a fatty powder. The mixture is transferred to a tray and is allowed to harden. When completely hard and dry, it is sifted through a No. 16 screen and is transferred to the Hobart mixer. The dextrose monohydrate and vanilla flavor are added and the mixture is mixed for three minutes.

| Premix II (Pretreatment of Antacid Material for Improved Palatibility) | Parts by Weight of Total Tablet |
|---|---|
| 8. CaCO$_3$ | 13 |
| 9. Al(OH)$_3$ | 5 |
| 10. Mg(OH)$_2$ | 4 |
| 11. Carboxymethyl cellulose | 0.75 |
| 12. Emulsifier (polyglycerol esters of fatty acids) (Santone 8-1-0) | 0.5 |
| 13. Vegetable oil (Durkex 500) | 0.5 |
| 14. Artificial vanilla flavor | 0.1 |

The above Premix II is prepared as follows.

In a Hobart mixer, the CaCO$_3$, Al(OH)$_3$, Mg(OH)$_2$ and carboxymethyl cellulose are dry blended. In a separate container, the Santone 8-1-0 (emulsifer), vegetable oil and vanilla flavor are mixed and the mixture is added slowly to the antacid/CMC mixture. Mixing is continued until a uniform free flowing powder is attained. Each antacid particle is coated with oil, flavor and emulsifier for saliva stimulation.

| Premix III (Pretreatment of Direct Compaction Tabletting Aids) | Parts by Weight of Total Tablet |
|---|---|
| 15. Dextrose monohydrate | 23 |
| 16. Tabletting sugar | 12.5 |
| 17. Artificial vanilla flavor | 0.4 |
| 18. Peppermint oil | 0.1 |

The dextrose monohydrate and tabletting sugar are dry blended in a Hobart mixer and the vanilla flavor and peppermint oil are added thereto with mixing for 5 minutes.

The Premixes I, II and III are now dry blended together in a mixer with an additional 0.5% carboxymethyl cellulose gum for 3.5 minutes. The resulting composition is then tabletted on a conventional tablet press.

It is found that the chewable antacid tablets of the invention prepared as described above are soft yet flexible. When dropped on a hard floor from a distance of 2.5 meters, the antacid tablets will not break, whereas prior art chewable tablets when dropped from such a height shatter upon striking a hard floor. Moreover, the so-formed chewable antacid tablet of the invention is significantly softer to bite through than prior art chewable tablets as indicated by the following "Durometer Readings" and "Tablet Hardness Readings".

| Durometer Readings (average 10 samples expressed in store units) | Force in lb. required to penetrate |
|---|---|
| Rolaids | 35.5 |
| Tums | 42.2 |
| Pepto Bismol | 38.2 |
| Flintstones Vitamins | 27.9 |
| Example 1 chewable antacid | 10.0 |

| Tablet Hardness Readings | Force required to shatter tablet through compression of diameter |
|---|---|
| Rolaids | 5.71 (avg. 5 readings) |

| | |
|---|---|
| Tums | 6.52 (avg. 5 readings) |
| Example 1 chewable antacid | 2.97 (avg. 10 readings) |

Furthermore, the chewable antacid tablet prepared as described above is found to have a non-chalky non-gritty pleasant taste which when exposed to saliva in the mouth converts to an emulsion or colloidal suspension and thus behaves as would a liquid.

EXAMPLE 2

A low calorie chewable antacid tablet is prepared as described in Example 1 except that one-half of the dextrose monohydrate is replaced by isomaltitol (Palatinit).

EXAMPLE 3

A chewable vitamin tablet having a final weight of 1 g is prepared as described in Example 1 except that Premix II (the active ingredient premix) is composed of:

| Ingredient | Per 250 mg (100% U.S.R.D.A.) |
|---|---|
| Vitamin C | 75 mg |
| Niacinamide | 22 mg |
| Pyridoxine hydrochloride | 2.9 mg |
| Riboflavin | 2 mg |
| Thiamine Mononitrate | 1.8 mg |
| Vitamin A | 6000 I.U. |
| Iron, Electrolytic | 20 mg |

EXAMPLE 4

A chewable aspirin tablet having a final piece weight of 3 g is prepared as described in Example 1 except that Premix II (the active ingredient Premix) is composed of salicylic acid. The chewable tablet will provide approximately 750 mg salicylic acid per dose.

EXAMPLE 5

A chewable analgesic tablet is prepared as described in Example 4 except that the active ingredient is acetaminophen.

What is claimed is:

1. A compressed chewable antacid tablet having good hardness and flexibility and easy bite-through which comprises a blend of (a) a particulate pretreated fat composition comprising an edible fatty material comprising hydrogenated tallow, hydrogenated vegetable oil, almond oil, coconut oil, corn oil, cottonseed oil, refined linseed oil, light liquid petrolatum, heavy liquid petrolatum, olein, olive oil, palm oil, peanut oil, persic oil, sesame oil, soybean oil or safflower oil, a fat sorbing material having the fatty material sorbed thereon or therein, the fat sorbing material comprising microcrystalline cellulose, cornstarch, tapioca, dextrin, sucrose, sorbitol, xylitol or mannitol, and one or more tablet bonders said tablet bonders comprising tabletting sugar, dextrose monohydrate or mixtures thereof, blended therewith or mixtures thereof with one or more antioxidants, flavors, colorant or mixtures thereof; (b) a pretreated active ingredient composition comprised of a mixture of particles of active ingredient which comprises an antacid, or mixtures thereof with edible oil, binder, emulsifier, flavor, colorant or mixtures thereof; the particles of active ingredient being coated with the other components of said pretreated active ingredient composition; and (c) a pretreated direct compaction tabletting aids composition comprising one or more tablet bonders comprising tabletting sugar, dextrose monohydrate or mixtures thereof, or mixtures thereof with flavors.

2. The compressed chewable tablet as defined in claim 1 wherein said antacid material comprises calcium carbonate, magnesium carbonate, magnesium hydroxide, aluminum hydroxide, or mixtures thereof.

3. The compressed chewable tablet as defined in claim 1 wherein said fatty material is employed in a weight ratio to said fat-sorbing material of from about 0.625:1 to about 1.875:1.

4. The compressed chewable antacid tablet as defined in claim 1 wherein the particulate pretreated fat composition (a) includes as a fat-sorbing material microcrystalline cellulose, hydrogenated vegetable oil as a fatty material absorbed in the microcrystalline cellulose, or mixtures thereof with a colorant or mixtures thereof with an antioxidant or mixtures thereof with an antiflatulent, tablet bonders comprising tabletting sugar, dextrose monohydrate or mixtures thereof or mixtures thereof with one or more flavors, the pretreated active ingredient composition (b) comprises particles of one or more antacids comprising calcium carbonate, aluminum hydroxide, magnesium hydroxide, or a mixture of all of said antacids, a binder, comprising carboxymethyl cellulose to help flavor and emulsifier to stick to fat-absorbed particles, and impart a slippery mouth feel, an emulsifier comprising polyglycerol ester of fatty acid to help decrease surface tension on the tongue and stimulate salivation, an edible oil comprising a vegetable oil to help plating out of the emulsifier on the antacid particles, and flavor, and the pretreated direct compaction tabletting aids composition comprises tablet bonders, comprising tabletting sugar, dextrose monohydrate or mixtures thereof, and flavors and flavor oils.

5. A method for forming a compressed chewable antacid tablet as defined in claim 1 which comprises forming a particulate pretreated fat composition by melting the edible fatty material, admixing the melted fatty material with colorant, and antioxidant, admixing the resulting mixture with the fat-sorbing material thereby causing the fatty material to be sorbed on the fat-sorbing material, the mixture at this juncture exhibiting the appearance of a fatty powder, allowing the resulting mixture to dry and harden, and after sifting the mixture, blending same with one or more tabletting bonders and flavors, to form the particulate pretreated fat composition (a);

forming the pretreated active ingredient composition (b) by blending particles of active ingredient and binder, separately blending together one or more emulsifiers, edible oil, and flavor, and blending each of the above mixtures until a free-flowing powder is obtained wherein said particles of active material are coated with binder, oil, flavor and emulsifer;

forming the pretreated direct compaction tabletting aids composition by mixing one or more tablet bonders with one or more flavors;

blending the above mixes; and forming a compressed tablet from the resulting mixture.

* * * * *